(12) United States Patent
Evans (10) Patent No.: US 8,858,207 B2
(45) Date of Patent: *Oct. 14, 2014

(54) TOTAL KNEE JOINT MOLD AND METHODS

(76) Inventor: Richard Parker Evans, Golden, CO (US)

(*) Notice: Subject to any disclaimer, the term of this patent is extended or adjusted under 35 U.S.C. 154(b) by 28 days.

This patent is subject to a terminal disclaimer.

(21) Appl. No.: 13/350,253

(22) Filed: Jan. 13, 2012

(65) Prior Publication Data

US 2012/0193509 A1 Aug. 2, 2012

Related U.S. Application Data

(63) Continuation of application No. 12/194,436, filed on Aug. 19, 2008, now Pat. No. 8,097,039, which is a continuation of application No. 10/714,050, filed on Nov. 14, 2003, now Pat. No. 7,427,296.

(51) Int. Cl.
*A61F 2/38* (2006.01)
*B29C 39/24* (2006.01)
*A61L 24/00* (2006.01)
*A61L 24/06* (2006.01)
*A61F 2/30* (2006.01)
*A61F 2/46* (2006.01)

(52) U.S. Cl.
CPC ... *A61L 24/0015* (2013.01); *A61F 2002/30672* (2013.01); *A61F 2002/30677* (2013.01); *A61F 2/30942* (2013.01); *A61L 2300/406* (2013.01); *A61F 2002/30878* (2013.01); *A61F 2002/30957* (2013.01); *A61F 2310/003553* (2013.01); *A61L 24/06* (2013.01); *A61F 2/38* (2013.01); *A61F 2002/4631* (2013.01); *A61F 2002/3069* (2013.01); *Y10S 623/901* (2013.01)

USPC ............ 425/2; 249/104; 249/127; 249/140; 249/154; 249/160; 623/20.15; 623/901; 264/222; 264/261; 264/336; 264/339

(58) Field of Classification Search
CPC ....... A61F 2/38; A61F 2/3886; B29C 43/021; B29K 2021/00
USPC ......... 249/54, 57, 59, 95, 102–104, 117, 127, 249/139, 140, 154, 160; 264/222, 249, 261, 264/274, 336, 339; 425/2; 623/20.14, 623/20.15, 901
See application file for complete search history.

(56) References Cited

U.S. PATENT DOCUMENTS

| | | | | |
|---|---|---|---|---|
| 2,505,507 A | * | 4/1950 | Sennholtz et al. | 164/18 |
| 2,642,009 A | | 6/1953 | Orfitelli | |
| 3,028,283 A | * | 4/1962 | Lundgren et al. | 264/245 |
| 3,161,917 A | * | 12/1964 | Wiland | 249/54 |
| 3,237,910 A | * | 3/1966 | Lavedas | 249/117 |
| 3,353,220 A | * | 11/1967 | Lenoble | 425/123 |

(Continued)

*Primary Examiner* — Dimple Bodawala
(74) *Attorney, Agent, or Firm* — Kilpatrick Townsend & Stockton LLP (57) ABSTRACT

In one embodiment, a method for treating an infected implant area of a knee joint comprises surgically accessing the implant area, and inserting a tibial component into the tibia using an antibiotic-impregnated material. A femoral component is formed that is configured to interact with the tibial component by stable knee joint articulation and motion. The femoral component is formed of an antibiotic-impregnated material using a mold. The femoral component is attached to the femur using an antibiotic-impregnated material, and the tibial component is interfaced with the femoral component to form a stable temporary knee joint capable of reducing the spread of infection while permitting movement of the knee joint.

3 Claims, 7 Drawing Sheets

(56) References Cited

U.S. PATENT DOCUMENTS

| | | | |
|---|---|---|---|
| 3,964,106 A * | 6/1976 | Hutter et al. | 623/20.19 |
| 4,209,861 A | 7/1980 | Walker et al. | |
| 4,247,075 A * | 1/1981 | Rogers | 249/95 |
| 4,898,359 A * | 2/1990 | Gopon | 249/54 |
| 4,938,906 A * | 7/1990 | Brault | 264/163 |
| 5,123,927 A * | 6/1992 | Duncan et al. | 623/20.21 |
| 5,171,282 A * | 12/1992 | Pequignot | 623/20.35 |
| 5,226,915 A | 7/1993 | Bertin | |
| 5,480,444 A | 1/1996 | Incavo | |
| 5,639,279 A | 6/1997 | Burkinshaw | |
| 5,980,573 A | 11/1999 | Shaffner | |
| 5,996,963 A * | 12/1999 | Michael | 249/54 |
| 6,013,103 A | 1/2000 | Kaufman et al. | |
| 6,342,075 B1 | 1/2002 | MacArthur | |
| 6,355,705 B1 | 3/2002 | Bond et al. | |
| 6,506,215 B1 | 1/2003 | Letot et al. | |
| 7,131,626 B2 * | 11/2006 | Cole | 249/115 |
| 7,427,296 B2 * | 9/2008 | Evans | 623/20.14 |
| 8,097,039 B2 * | 1/2012 | Evans | 623/20.14 |
| 8,123,813 B2 * | 2/2012 | Metzger et al. | 623/20.14 |
| 2005/0061947 A1 * | 3/2005 | Smirnov et al. | 249/140 |

\* cited by examiner

TOTAL KNEE JOINT MOLD AND METHODS

CROSS-REFERENCES TO RELATED APPLICATIONS

This application is a continuation of U.S. patent application Ser. No. 12/194,436, filed Aug. 19, 2008, which is a continuation of U.S. application Ser. No. 10/714,050, filed Nov. 14, 2003, the complete disclosure of which is herein incorporated by reference.

BACKGROUND OF THE INVENTION

This invention relates generally to the field of orthopedic surgery, and in particular to total knee replacements. More specifically, the invention relates to the treatment of an infected total knee replacement.

In the United States, about 600,000 total knee arthroplasty procedures (also known as total knee replacements) are performed each year. A typical total knee replacement procedure involves resurfacing of the tibial plateaus and the femoral condoyle. Holes are then drilled into the femur and the tibia. A metallic femoral component is then inserted into the femur and a metallic tibial component is inserted into the tibia. Bone cement usually holds the two components into place. These two components work together to replace the diseased knee joint and to simulate the function of a normal knee joint. One example of a total knee replacement surgery is described in U.S. Pat. No. 6,342,075, the complete disclosure of which is herein incorporated by reference.

About two to three percent of total knee replacements become deeply infected. When these components are simply be replaced by new components the rate of cure of the infection is low compared to a two-stage surgical treatment where the components are removed and the infection treated before new components are reimplanted. In such cases, some have proposed removing the femoral and tibial components and replacing them with a puck-shaped spacer or void shaped spacer made of bone cement that is impregnated with an antibiotic or a fixed mass of antibiotic impregnated cement that fills the dead space left by the removal of the infected prosthetic components. This is placed between the femur and the tibia for six to twelve weeks. The antibiotic in the puck or cement mass leaches out over time to treat the infection. When the infection is contained, the puck is removed and the femoral and tibial components are once again inserted. Such a process is described in U.S. Pat. No. 5,980,573, the complete disclosure of which is herein incorporated by reference.

One problem with the use of such a spacer is that there is no knee joint while the infection is being treated. As such, the leg cannot move or bend. Often the spacer is loose and painful and the knee will scar down and will stiffen up, resulting in painful rehabilitation, loss of final normal range of motion and function, among other ailments. This also makes the final replacement surgery itself technically more difficult because of the scarring and loss of motion and knee joint space at the time of reimplantation of new permanent components

SUMMARY OF THE INVENTION

In one embodiment, the invention provides a method for treating an infected implant area of a knee joint. According to the method, the implant area is surgically accessed and any infected total knee replacement implants are removed from the implant area. This is completed with an aggressive surgical debridement of all infected tissue. A standard posterior stabilized all polyethylene tibial component is inserted temporarily into the tibia and is secured using antibiotic-impregnated bone cement. A femoral component is sized and then formed, preferably during the surgery, of antibiotic-impregnated bone cement. To do so, a mold may be used to form the femoral component into the appropriate shape. The femoral component is temporarily attached to the femur using antibiotic-impregnated bone cement. The tibial component is interfaced with the femoral component to form a temporary knee joint capable of eluting high levels of antibiotics thus treating and reducing the spread of infection while permitting movement of the knee joint. In this way, the infection may be treated by local antibiotic elution as well as intravenous antibiotic elution while also providing movement of the leg at the knee joint. In this way, stiffening of the leg is generally prevented and knee joint range of motion is preserved thereby reducing pain during treatment and allowing more functional activity of daily living during the recovery time. This also improves the technical ease and success of the final operation of revision knee component implantation and the ultimate outcome of improved knee joint range of motion and overall function of the final knee replacement.

In one aspect, the tibial component may comprise a generally smooth articulating element that interfaces with the femoral component to minimize wear debris from the femoral component. For example, the tibial component may be constructed of polyethylene. In this way, the amount of wear experienced by the femoral component may be reduced as it interacts with the tibial component. Also, the femoral component is constructed so that it interfaces with the tibial component to stabilize the knee joint, thereby facilitating movement while the infection is being treated.

To form the femoral component, one or more powdered antibiotics may be combined with a polymer in powder form. A liquid activating agent is added to the mixture to form the antibiotic-impregnated material. The resulting antibiotic-impregnated material is like dough, and is placed into the mold where it is formed into the shape of the femoral component. The size of the component required is determined at surgery. Once shaped, the mold is removed and the femoral component is permitted to harden. If needed, edges of the femoral component may be trimmed. Preferably, the femoral component is formed into the shape of an articulating femoral prosthesis. The femoral and tibia components are temporarily secured to the bone using antibiotic-impregnated bone cement. In this way, the antibiotic leaches out to treat the infection. Before the components are attached to the bone, however, the bone cement is allowed to partially cure so that bone cement does not significantly interdigitate with the bone and so the components may be removed without damaging the bone.

After the infection has subsided and determined to be infection free, the implant area may be re-accessed, and the femoral and tibial components may be removed and replaced with a permanent femoral prosthesis and a tibial prosthesis. Because the bone cement was allowed to partially cure, the components may easily be removed.

In another embodiment, the invention provides a temporary knee prosthesis that comprises a femoral component comprising an antibiotic impregnated bone cement that is formed in the shape of a femoral knee joint using a mold. The bone cement is placed into the mold, permitted to harden and then removed from the mold. In one aspect, the bone cement may comprise a polymethylmethacrylate material combined with an antibiotic. This bone cement allows the antibiotic to elute from the bone cement at higher levels than can be obtained from the standard and simultaneous intravenous antibiotic administration that is administered routinely for four to six weeks. The antibiotics eluted also penetrate and treat avascular tissue that intravenous antibiotics cannot reach, thus increasing the overall success rate of the two stage treatment over a simple one stage exchange of components. Such a mold provides the appropriate geometrical shape of the femoral component that allows articulation and movement of the knee joint during the treatment period. Additionally the femoral component made from such a mold provides a smooth surface on the femoral component which decreases friction of the femoral component and tibial component articulation or movement during the treatment period. This smooth geometric shape formed by the mold allows a greater range of motion of the knee to be maintained during treatment and decreases friction of the components and therefore the wear debris of the femoral and tibial articulation during movement in the treatment period. This is desirable because the wear debris cannot often be entirely removed at the final stage of surgery and becomes a residual foreign body that may aggravate treatment of the infection or even become a focus of a new infection after the antibiotics have eluted from the cement debris.

The femoral component may be part of a kit that also includes a tibial component that is made of a smooth material, such as a polyethylene, to prevent wear of the femoral component. A posterior stabilized tibial component configuration adds knee joint stability to the knee motion during treatment.

DESCRIPTION OF THE SPECIFIC EMBODIMENTS

The invention provides exemplary techniques and kits that may be used to treat an infected implant area resulting from a total knee replacement procedure. Following diagnosis of the infection, the implant area needs to be surgically accessed. This may be accomplished by forming a long incision on the front of the knee to expose the previously inserted femoral and tibia prostheses that form the knee replacement. This incision is typically through the scar of the original component implantation procedure. All infected total knee replacement implants are removed and a radical soft and hard tissue debridement is performed.

The implants are replaced with temporary implants that are used to fight the infection. One of the implants may be constructed of bone cement impregnated with an antibiotic while the other is made of a material that interfaces with the bone cement implant without causing excessive wear of the bone cement implant. This may be done during the surgical procedure to permit the surgeon to determine the proper size of the implant while the femur and the tibia are exposed. Both implants may be temporarily attached to the femur and the tibia using the antibiotic impregnated bone cement to help fight the infection. In so doing, the bone cement is allowed to sufficiently cure or harden so that the cement does not excessively interdigitate with the bone when the temporary components are inserted. Thus when the implants are subsequently removed, the bone cement will not tear away excessive bone and other tissue. Also, the implants are configured in a shape that permits movement of the leg at the knee joint while also providing stability, posterior as well as medial and lateral. This permits stable movement in the leg to help prevent the leg from stiffening up while the temporary implants are in place. Once the infection has been treated, the knee is again opened, the temporary implants are removed and permanent knee replacement implants are put back in. As just described, by allowing the bone cement to somewhat harden before attaching the implants to the femur and the tibia, the implants may easily be removed without damaging the tissue and preserving the bone stock needed to perform adequate revision implantation of permanent components. In this way, the new revision knee replacement prosthetics may more easily be attached and implanted, thereby reducing surgery time and improving the final outcome per standard total joint replacement analysis.

Figure 1:
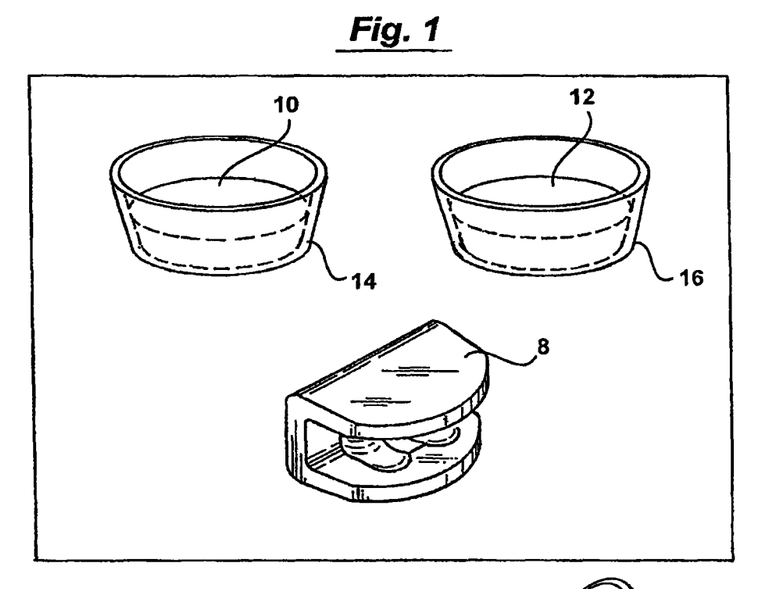
FIG. 1 illustrates a kit that may be used to make a femoral component when treating an infected area associated with a total knee replacement according to the invention.

Referring now to the figures, one exemplary method for performing such a procedure will be described. In FIG. 1, an incision has already been made in the patient's knee and the knee joint implants have been removed. The temporary femoral component is ready to be produced using a mold 8. This process utilizes an antibiotic impregnated material. This is made from two anesthetic agents 10 and 12 that are stored within containers 14 and 16. For example, agent 10 may comprise one kind of antibiotic while component 12 may comprise another kind of antibiotic. Conveniently, agent 10 may comprise of powdered tobramycin, and agent 12 may comprise of powdered vancomycin, commercially available from several pharmaceutical companies. However it will be appreciated that other types of antibiotics may be used as well if they are heat stable, elute from the bone cement and are desired to more specifically treat a given infectious organism that has been identified.

Figure 2:
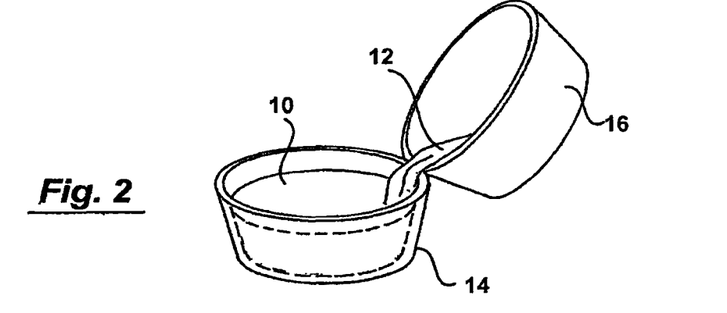
FIG. 2 illustrates a method for dividing an antibiotic/bone cement powder according to the invention.
Figure 3:
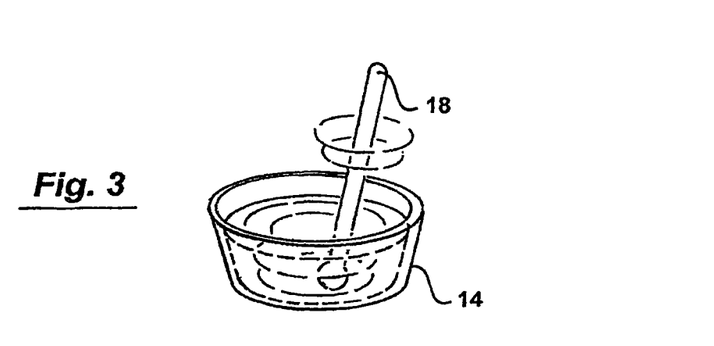
FIG. 3 illustrates a method for mixing the antibiotic with the bone cement.

As shown in FIG. 2, agents 10 and 12 are combined and powdered bone cement is also added. Often the antibiotics obtained are granular and can be made into a finer powder once again by pushing the powder through a standard commercially available cement screen. These are mixed with the bone cement which is also in powder form, and is a methylmethacrylate polymer, commercially available from a number of companies. It should be stated that Palacos bone cement, commercially available from has been shown to have the best antibiotic elution characteristics by a number of studies and is the preferred bone cement to use. The ingredients are mixed together using a stirrer 18 as shown in FIG. 3. The mixture may then be divided by pouring half back into container 14 for later use as described hereinafter.

Figure 4:
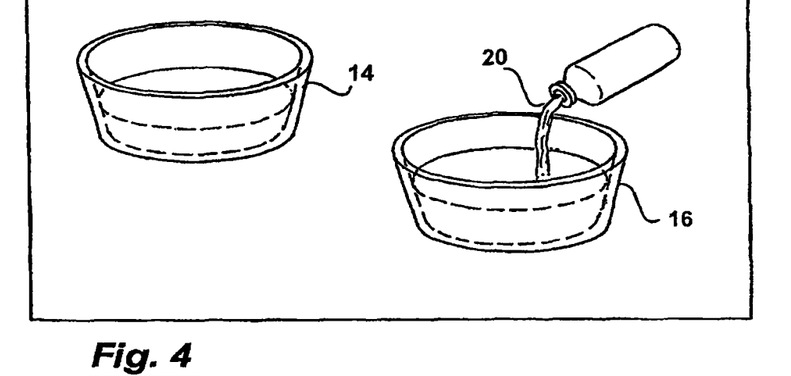
FIG. 4 illustrates a method for adding an activating agent to the antibiotic/bone cement mixture.
Figure 5:
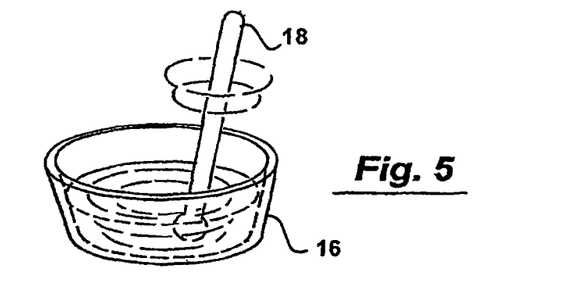
FIG. 5 illustrates a method for mixing the activating agent with the bone cement mixture.

In FIG. 4, an activating agent 20 (the monomer universally provided with each bone cement kit from all companies) is added to the mixture and reacts with the bone cement to form polymethylmethacrylate 22 (also referred to as PMMA). The mixture is stirred with stirrer 18 until the PMMA 22 has a doughy consistency as shown in FIG. 5. Although described using one type of bone cement with specific types of antibiotics, it will be appreciated that other bone cements and antibiotic agents may be used, including those described in U.S. Pat. No. 6,355,705, the complete disclosure of which is herein incorporated by reference.

Figure 6:
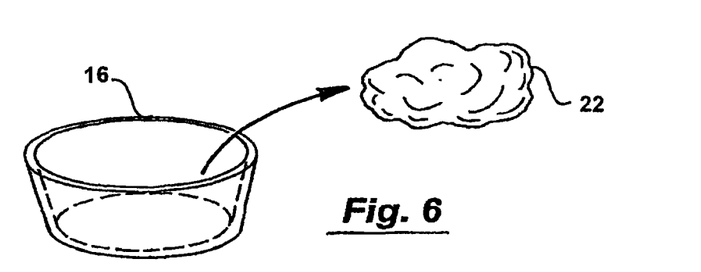
FIGS. 6 and 7 illustrates a method for shaping the resulting bone cement.
Figure 7:
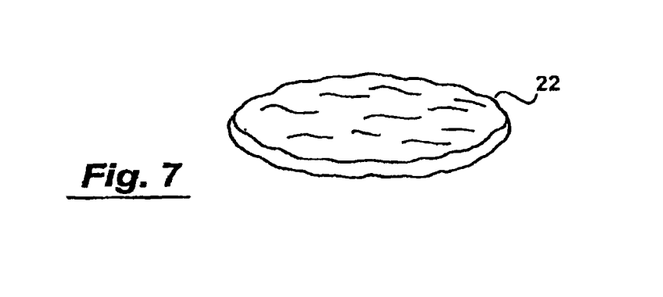
Figure 8:
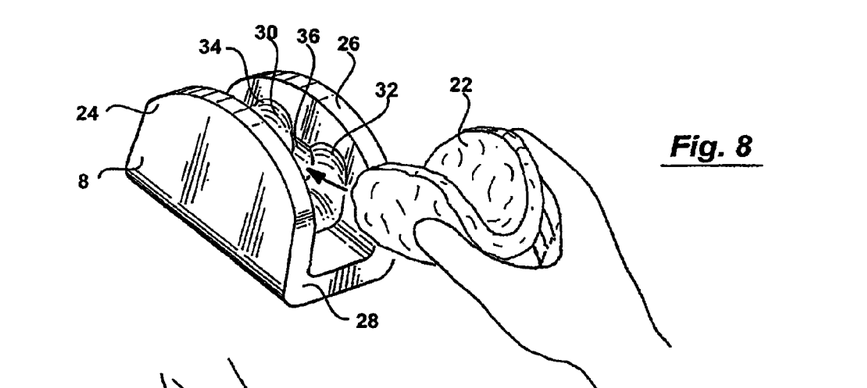
FIG. 8 illustrates the placement of the bone cement into a mold.

In FIG. 6, the PMMA 22 is removed from container 16 and formed into a pancake shape as shown in FIG. 7. The PMMA 22 is then placed into mold 8 as shown in FIG. 8. Mold 8 has a pair of sides 24 and 26 and a bottom 28, and is constructed of a flexible material, such as a medical grade plastic to permit sides 24 and 26 to be flexed away from each other. Formed in mold 8 is a cavity 30 that is in the shape of the exterior of a traditional femoral prosthesis 15 modified (thickened throughout) to provide greater strength to the cement femoral component. As shown, cavity 30 includes two depressed two outer arched sections 32 and 34 and an inner section 36. The inner section is vertically below the bottom of the U-shaped back surface such that the center section of the resulting femoral component is formed when the antibiotic-impregnated material is placed into the cavity. The two outer arched sections 32 and 34 are transverse to the sides 24 and 26 and a longitudinal axis of the mold. This configuration is used to produce a femoral component 40 that interfaces with a tibial component 42 as described hereinafter (see FIG. 12). However, it will be appreciated that other shapes of femoral components may be produced as well, including those known in the art and those described in U.S. Pat. Nos. 5,226,915 and 6,506,215, the complete disclosures of which are herein incorporated by reference.

Figure 9:
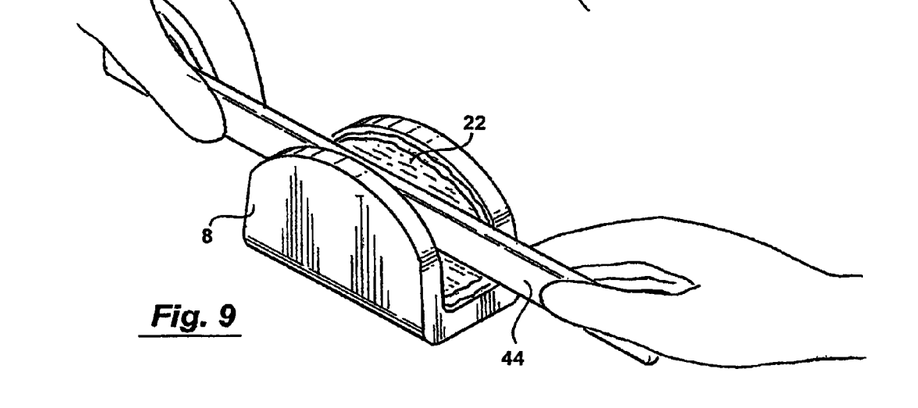
FIG. 9 illustrates how the bone cement is formed in the mold.
Figure 10:
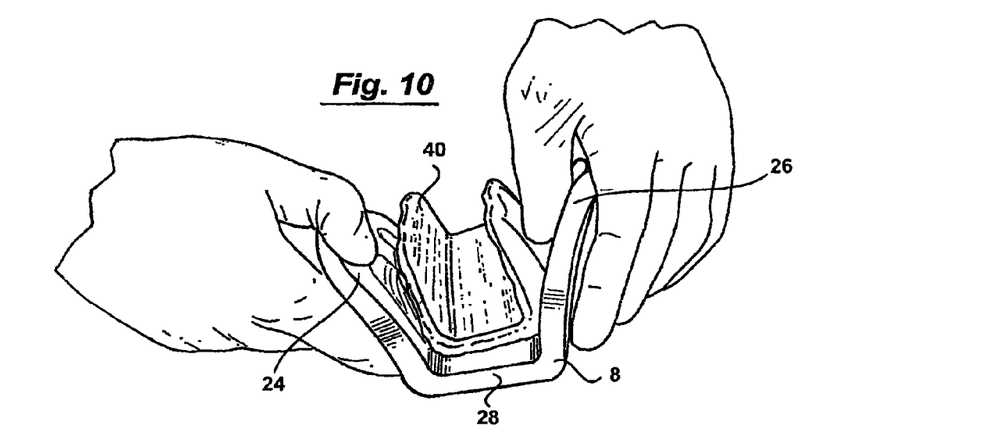
FIG. 10 illustrates the removal of the resulting femoral component from the mold.
Figure 11:
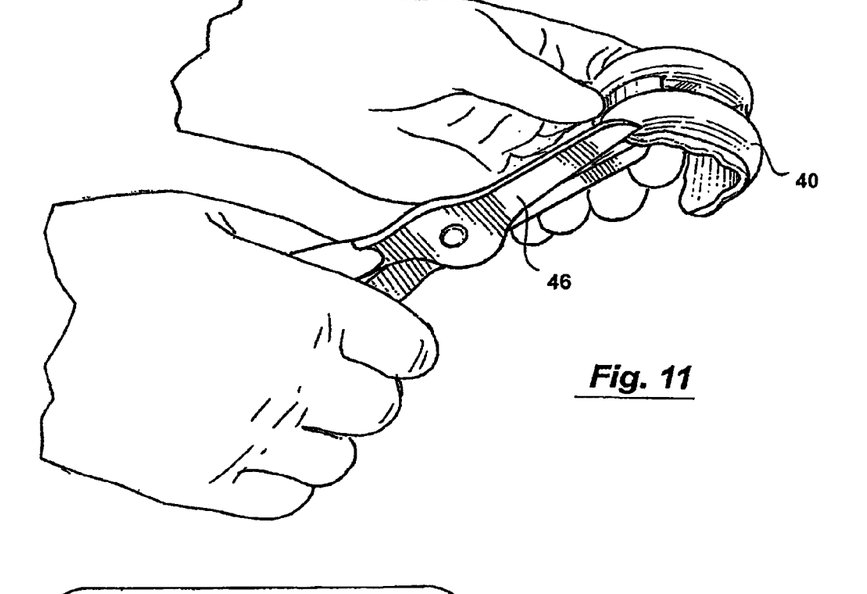
FIG. 11 illustrates the removal of excess material from the femoral component.

As shown in FIG. 9, the PMMA 22 is pressed into cavity 30 and a straight edge 44 is used to smooth the back side of the PMMA 22. Once formed in the desired shape, sides 24 and 26 are pulled away from each other as shown in FIG. 10 to permit the femoral component 40 to be removed from mold 8. When removed from mold 8, femoral component 40 is still somewhat soft to permit any unwanted edges to be trimmed using scissors 46 as shown in FIG. 11. The approximate time from mixing to removal from the mold is about three minutes to about ten minutes depending on the cement used, the amount and type of antibiotics mixed into the cement and the room temperature. Femoral component 40 is typically hard enough to be attached to the femur after about five minutes to about fifteen minutes from the time of mixing.

Figure 12:
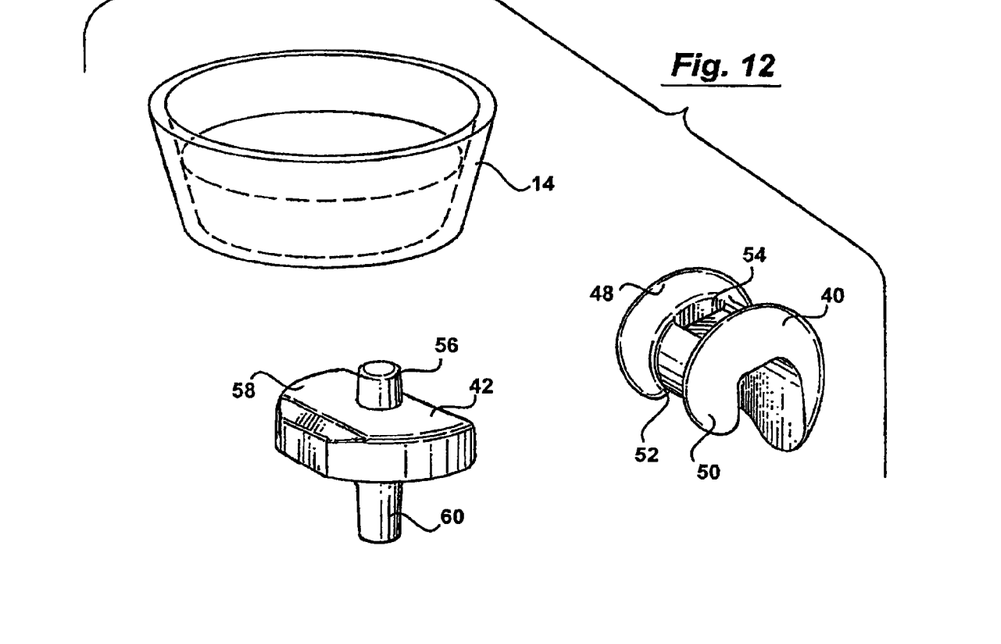
FIG. 12 illustrates the femoral component of FIG. 11 along with a tibial component.

As best shown in FIG. 12, femoral component has two outer rails 48 and 50 and a center section 52. Formed in center section 52 is a recess 54 for receiving the posterior stabilizing protrusion 56 on tibial component 42. Tibial component 42 also includes a tray 58 and a central stem 60 that fits within the tibia. In use, protrusion 56 fits within recess 54 and rails 48 and 50 sit on tray 58. In this way, femoral component 40 and tibial component 42 may articulate with respect to each other while providing posterior as well as lateral and medial stability to the knee joint. Tibial component 42 may also be constructed of a material that will not cause excessive wear on femoral component 40. Examples of materials include polyethylene. Hence, when the two components are interfaced with each other, the knee joint may articulate without degrading or breaking the relatively fragile femoral component 40. This permits the patient to be able to articulate the leg while the infection is being treated.

Figure 13:
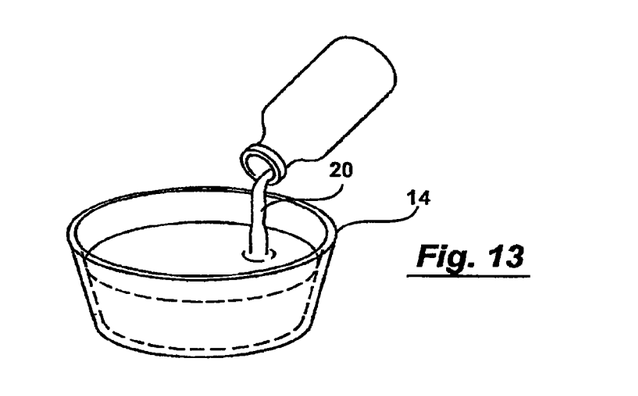
FIGS. 13 and 14 illustrate a method for making more antibiotic impregnated bone cement.
Figure 14:
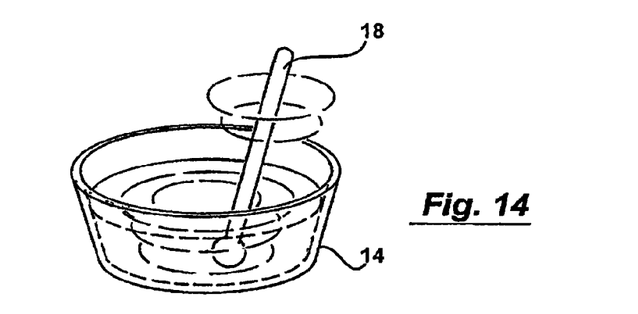

With femoral component 40 sufficiently hardened, it is ready to be attached to the femur. To do so, container 14 which holds the reserved half of the antibiotic-laden bone cement is combined with activating agent 20 as shown in FIG. 13. This is then mixed with stirrer 18 (see FIG. 14) in essentially the same was as previously described to provide more PMMA. At this point, timing is critical. The PMMA will be used both to attach tibial component 42 to the tibia and femoral component 40 to the femur. However, since both of these components will be removed once the infection has been treated (in about 6 to 12 weeks); they need to be cemented in such a way that they can be removed without causing significant tissue damage. As such, the PMMA 22 is allowed to cure to the point where it still has adhesive qualities, but yet does not provide excessive bonding or bone recess interdigitation so that the two prostheses may easily be removed and replaced with their permanent counterparts. Typically, the PMMA 22 will be used within a window of about two minutes to about five minutes after mixing again depending on the cement type used, the amount and type of antibiotics mixed into the cement and the room temperature.

Figure 15:
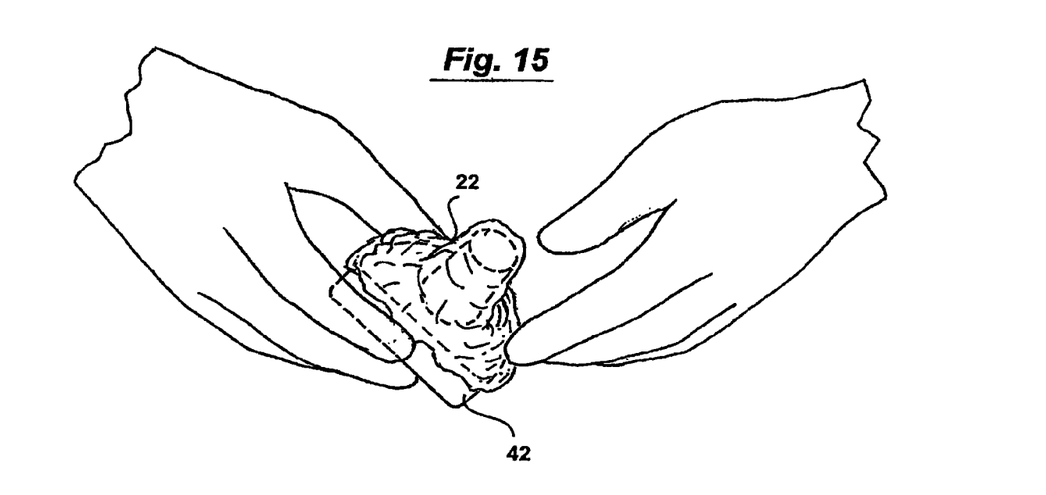
FIG. 15 illustrates a method for placing the bone cement onto the tibial component.
Figure 16:
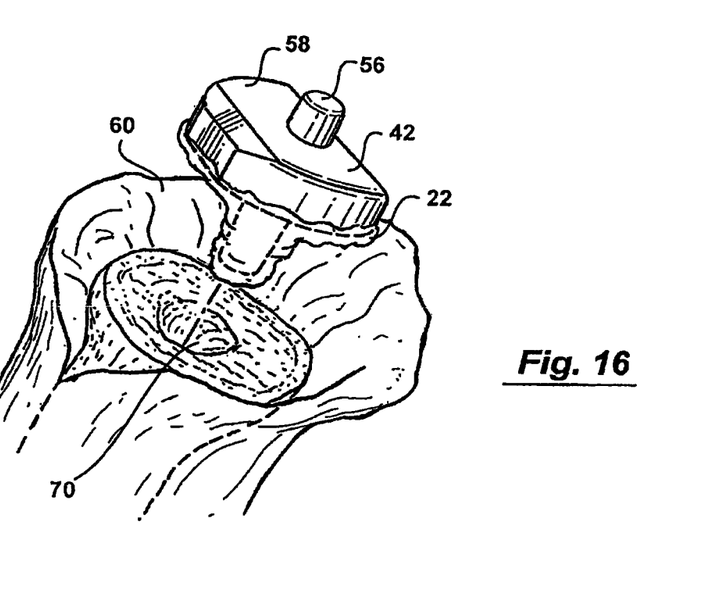
FIGS. 16 and 17 illustrate a method for inserting the tibial component into the tibia.
Figure 17:
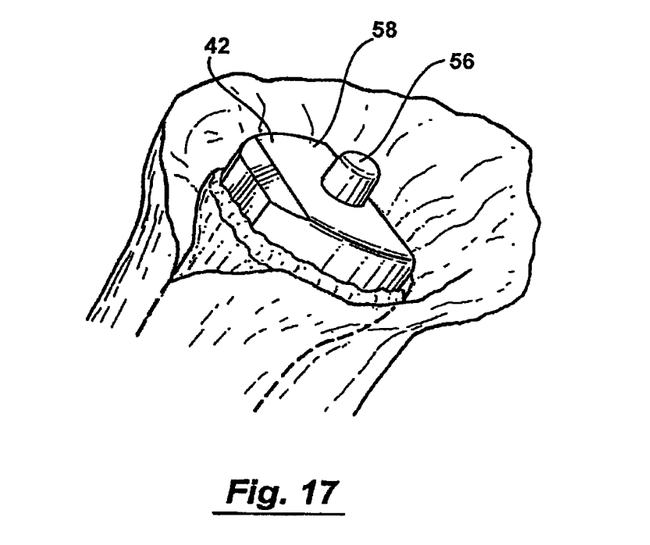

As shown in FIG. 15, the semi-cured PMMA 22 is formed around stem 60 and the bottom of tray 58 to a thickness of about one quarter inch to about one half inch. At this point, the PMMA 22 is quickly setting and the surgeon is just able to form it around stem 60. As shown in FIGS. 16 and 17, tibial component 42 and the applied antibiotic cement are pressed into the tibia, with stem 60 extending into the intramedullary canal 70. Excess cement extrude during the insertion process is removed.

Figure 18:
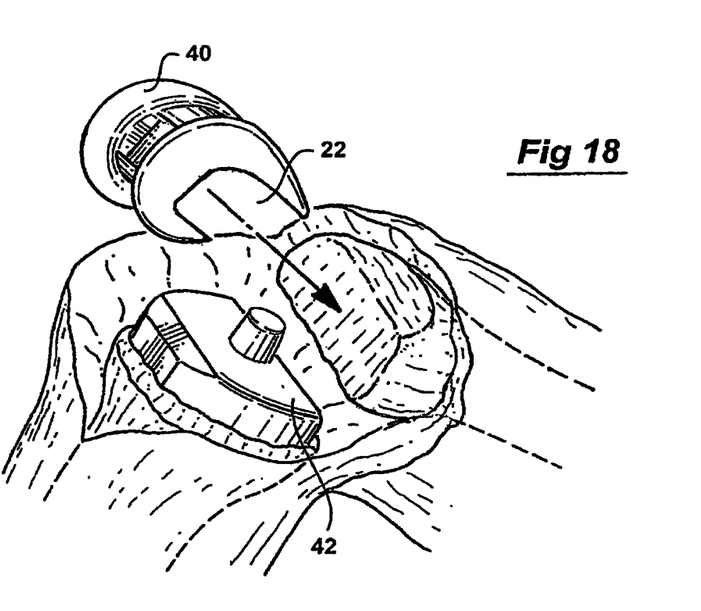
FIG. 18 illustrates a method for attaching the femoral component to the femur using bone cement.
Figure 19:
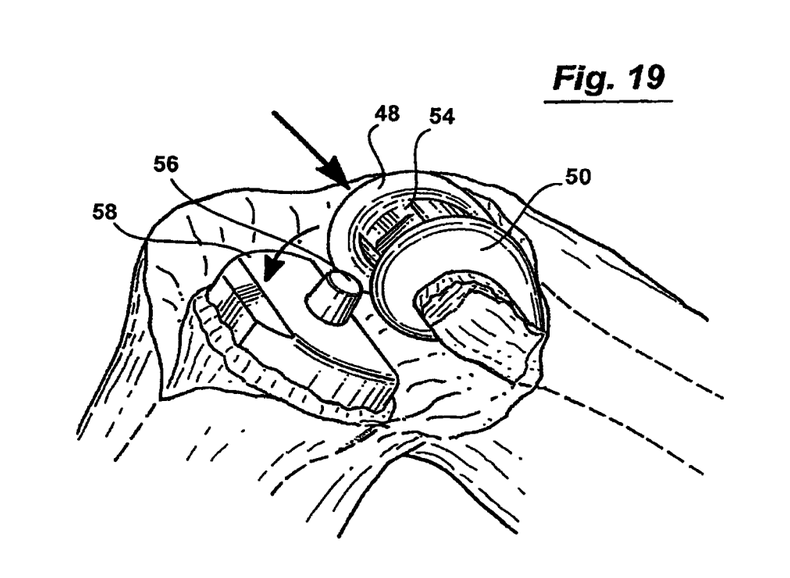
FIG. 19 illustrates the step of interfacing the tibial component with the femoral component.

More of the semi-cured PMMA 22 is also placed on the back side of femoral component 40 to a thickness of about one quarter inch to about one half inch as shown in FIG. 18. Femoral component 40 is then placed over the bottom of the femur as shown in FIG. 19. The protrusion 56 is then immediately placed into recess 54 and the leg is straightened so that rails 48 and 50 may roll over tray 58. Excess cement extrude during the insertion process is removed. The incision is then closed. The surgeon can and should move the knee prior to and after wound closure to ensure adequate articulation occurs as planned.

The patient should be able to and is encouraged to bend the leg at the knee. This helps to prevent the build up of scar tissue and the leg from stiffening. As previously described, the two components provide stability to the knee joint to facilitate its articulation. The bone cement used to form the femoral component 40 as well as the bone cement used to attach the two components to the tibia and the femur leach out over time to fight the infection. Although the femoral component can withstand the weight of the patients leg and forces concomitant to normal activities of daily living the cement femoral component may not be strong enough to withstand full weight bearing and the patient is discouraged to do so. Rather the patient uses ambulatory aides such as crutches or a walker until the second surgery when permanent components are implanted.

Once the infection has been treated, the knee may again be opened and the femoral component 40 and the tibial component 42 removed. As previously mentioned, the bone cement used to attach the two components to the bone was semi-cured, permitting the two components to easily be pulled from the bone without causing significant damage. The previously removed knee joint prosthesis may then be replaced with revision total knee components as is known in the art. Because little or no damage was caused by the temporary prostheses and because joint space and range of motion was maintained this process is relatively easy and comparable to a noninfected one stage revision knee replacement typically performed for component loosening or mechanical failure.

The invention has now been described in detail for purposes of clarity and understanding. However, it will be appreciated that certain changes and modifications may be practiced within the scope of the appended claims.

What is claimed is:

1. A mold for forming a femoral component using an antibiotic-impregnated material, the mold comprising: a smooth U-shaped back surface, wherein the U-shaped back surface comprises two spaced-apart inner side walls and a bottom, and wherein a recess for receiving the antibiotic-impregnated material is formed in the bottom and two inner side walls so as to continuously extend from a first of the two sidewalls through the bottom to a second of the two sidewalls, wherein the recess contains two depressed outer arched sections that are spaced apart from each other by an inner section, wherein the outer arched sections are transverse to a longitudinal axis of the mold, whereby the resulting femoral component comprises a one-piece structure having two outer surfaces that are spaced apart from each other by a center section, and wherein the femoral component includes a front surface that is configured to interface with a tibial component and a back surface that is configured to interface with a femur.

2. A mold as in claim 1, wherein the recess is vertically below the bottom of the U-shaped back surface such that the center section of the resulting femoral component is formed when the antibiotic-impregnated material is placed into the recess.

3. A mold for forming a femoral component using an antibiotic-impregnated material, the mold comprising: a smooth U-shaped back surface with a recess for receiving the antibiotic-impregnated material, wherein the recess contains two depressed outer arched sections that are spaced apart from each other by an inner section, wherein the U-shaped back surface comprises two spaced-apart inner side walls and a bottom, wherein the outer arch sections are transverse to the inner side walls, wherein the recess is formed in the bottom and two sidewalls so as to continuously extend from a first of the two sidewalls through the bottom to a second of the two sidewalls, and wherein the inner section is vertically below the bottom of the U-shaped back surface such that the center section of the resulting femoral component is formed when the antibiotic-impregnated material is placed into the recess, whereby the resulting femoral component comprises a one-piece structure having two outer surfaces that are spaced apart from each other by a center section, and wherein the femoral component includes a front surface that is configured to interface with a tibial component and a back surface that is configured to interface with a femur.

* * * * *